(12) United States Patent
Beens

(10) Patent No.: US 9,640,869 B2
(45) Date of Patent: May 2, 2017

(54) COPLANAR ANTENNA

(71) Applicant: WiseWear Corporation, San Antonio, TX (US)

(72) Inventor: Jason A. Beens, Helotes, TX (US)

(73) Assignee: WISEWEAR CORPORATION, San Antonio, TX (US)

( * ) Notice: Subject to any disclaimer, the term of this patent is extended or adjusted under 35 U.S.C. 154(b) by 0 days.

(21) Appl. No.: 14/789,704

(22) Filed: Jul. 1, 2015

(65) Prior Publication Data

US 2017/0005411 A1    Jan. 5, 2017

(51) Int. Cl.
*H01Q 9/04* (2006.01)
*A61B 5/00* (2006.01)

(52) U.S. Cl.
CPC ......... *H01Q 9/0407* (2013.01); *A61B 5/0024* (2013.01); *A61B 5/681* (2013.01); *H01Q 9/0442* (2013.01)

(58) Field of Classification Search
CPC .......... H01Q 1/38; H01Q 1/243; A61B 5/681; A61B 5/0002
USPC ......................................................... 343/702
See application file for complete search history.

(56) References Cited

U.S. PATENT DOCUMENTS

| | | | | |
|---|---|---|---|---|
| 6,741,214 B1* | 5/2004 | Kadambi | ............. | H01Q 9/0421 343/700 MS |
| 7,079,079 B2* | 7/2006 | Jo | ......................... | H01Q 1/243 343/700 MS |
| 2008/0204328 A1* | 8/2008 | Nissinen | .................. | H01Q 1/38 343/700 MS |
| 2010/0149751 A1* | 6/2010 | Camacho | ............. | G06F 1/1616 343/700 MS |
| 2012/0274508 A1* | 11/2012 | Brown | .................... | G04F 10/00 342/357.25 |
| 2013/0154897 A1* | 6/2013 | Sorensen | ............... | H01Q 7/005 343/861 |
| 2015/0255871 A1* | 9/2015 | Baringer | .............. | A61B 5/0002 343/702 |

* cited by examiner

*Primary Examiner* — Dameon E Levi
*Assistant Examiner* — Hasan Islam
(74) *Attorney, Agent, or Firm* — H. Barrett Spraggins; Kennedy Lenart Spraggins LLP

(57) ABSTRACT

In a particular embodiment of the present disclosure, a coplanar antenna includes a conductive plane having a first dimension and a second dimension, wherein the length of the conductive plane along the first dimension is less than one-quarter of a wavelength of a resonant frequency; an insulating region disposed within the conductive plane, wherein the insulating region is of a shape that outlines a conductive peninsula, wherein: the conductive peninsula is coupled to the conductive plane; the conductive peninsula is substantially coplanar to a major portion of the conductive plane; the conductive peninsula is electrically coupled to an electric feed circuit such that an impedance associated with the conductive peninsula when electrically coupled substantially matches a signal impedance at the electrical feed circuit; and the conductive peninsula is operable to resonate at the resonant frequency after receiving a current from the electric feed circuit.

9 Claims, 8 Drawing Sheets

600

Form a conductive plane from a first conductive material, the conductive plane having a first dimension and a second dimension, wherein the length of the conductive plane along the length of the conductive plane along the first dimension is less than one-quarter of a wavelength of a resonant frequency
602

Form a conductive peninsula from a second conductive material, the conductive peninsula being coupled to the conductive plane and separated from the conductive plane by an insulating region, wherein the conductive peninsula is substantially coplanar to a major portion of the conductive plane
604

Electrically couple the conductive peninsula to an electric feed circuit, wherein the conductive peninsula is operable to electrically couple a tunable inductance to the conductive plane after receiving a current from the electric feed circuit
606

Form a conductive plane from a first conductive material, the conductive plane having a first dimension and a second dimension, wherein the length of the conductive plane along the length of the conductive plane along the first dimension is less than one-quarter of a wavelength of a resonant frequency
702

Form a conductive peninsula from a second conductive material, the conductive peninsula being coupled to the conductive plane and separated from the conductive plane by an insulating region, wherein the conductive peninsula is substantially coplanar to a major portion of the conductive plane
704

Electrically couple the conductive peninsula to an electric feed circuit, wherein the conductive peninsula is operable to substantially resonate at a frequency after receiving a current from the electric feed circuit
706

FIG. 7

COPLANAR ANTENNA

BACKGROUND OF THE INVENTION

Field of the Invention

The field of the invention is coplanar antennas.

Description of Related Art

Personal, wearable technology continues to evolve, and the technologies underlying these wearable devices also continue to evolve. Some existing technologies incorporate antennas that require the use of an insulating radome over the antenna in order to both protect the underlying antenna from static discharge and to protect the electrical properties of the antenna itself.

SUMMARY OF THE INVENTION

In a particular embodiment of the present disclosure, a coplanar antenna includes a conductive plane having a first dimension and a second dimension, wherein the length of the conductive plane along the first dimension is less than one-quarter of a wavelength of a resonant frequency; an insulating region disposed within the conductive plane, wherein the insulating region is of a shape that outlines a conductive peninsula, wherein: the conductive peninsula is coupled to the conductive plane; the conductive peninsula is substantially coplanar to a major portion of the conductive plane; the conductive peninsula is electrically coupled to an electric feed circuit such that an impedance associated with the conductive peninsula when electrically coupled substantially matches a signal impedance at the electrical feed circuit; and the conductive peninsula is operable to resonate at the resonant frequency after receiving a current from the electric feed circuit.

In a particular embodiment of the present disclosure, a method for operating a coplanar antenna includes receiving a plurality of environmental data from a plurality of sensors; providing a current to a conductive plane, the conductive plane having a first dimension and a second dimension, wherein the length of the conductive plane along the first dimension is less than one-quarter of a wavelength of a resonant frequency; providing an electric signal from an electric feed circuit to a conductive peninsula electrically coupled to the electric feed circuit such that an impedance associated with the conductive peninsula when electrically coupled substantially matches a signal impedance at the electrical feed circuit, wherein the conductive peninsula is of a shape outlined by an insulating region disposed within the conductive plane, wherein: the conductive peninsula is coupled to the conductive plane; the conductive peninsula is substantially coplanar to a major portion of the conductive plane; and the conductive peninsula is operable to resonate at the resonant frequency after receiving the electric signal from the electric feed circuit; and transmitting data associated with the plurality of environmental data through an antenna circuit, the antenna circuit comprising the conductive plane and the conductive peninsula.

In a particular embodiment of the present disclosure, a personal sensor bracelet includes a curved conductive band comprising: a substantially planar portion having a first end and a second end; a first curved portion extending from the first end of the substantially planar portion; a second curved portion extending from the second end of the substantially planar portion; a coplanar antenna disposed, the coplanar antenna comprising: a conductive plane having a first dimension and a second dimension, wherein the length of the conductive plane along the first dimension is less than or equal to one-quarter of a wavelength of a resonant frequency, wherein a major portion of the conductive plane is disposed within the substantially planar portion; an insulating region disposed within the conductive plane, wherein the insulating region is of a shape that outlines a conductive peninsula, wherein: the conductive peninsula is coupled to the conductive plane; the conductive peninsula is substantially coplanar to the major portion of the conductive plane; the conductive peninsula is electrically coupled to an electric feed circuit such that an impedance associated with the conductive peninsula when electrically coupled substantially matches a signal impedance at the electrical feed circuit; and the conductive peninsula is operable to resonate at the resonant frequency after receiving a current from the electric feed circuit; a processor disposed within the substantially planar portion, the processor electrically coupled to the electric feed circuit; and a plurality of sensors disposed within the substantially planar portion, the plurality of sensors electrically coupled to the processor; a second curved band coupled to the curved conductive band such that the second curved band and the curved conductive band form a bracelet, wherein the second curved band is removably coupled to the curved conductive band at an end of the first curved portion distal from the substantially planar portion, and the second curved band is removably coupled to the curved conductive band at an end of the second curved portion distal from the substantially planar portion.

In a particular embodiment of the present disclosure, a method of manufacturing a coplanar antenna circuit includes forming a conductive plane from a first conductive material, the conductive plane having a first dimension and a second dimension, wherein the length of the conductive plane along the first dimension is less than one-quarter of a wavelength of a resonant frequency; forming a conductive peninsula from a second conductive material, the conductive peninsula being coupled to the conductive plane and separated from the conductive plane by an insulating region, wherein the conductive peninsula is substantially coplanar to a major portion of the conductive plane; and electrically coupling the conductive peninsula to an electric feed circuit, wherein the conductive peninsula is operable to resonate at the resonant frequency after receiving a current from the electric feed circuit.

The foregoing and other objects, features and advantages of the invention will be apparent from the following more particular descriptions of example embodiments of the invention as illustrated in the accompanying drawings wherein like reference numbers generally represent like parts of example embodiments of the invention.

BRIEF DESCRIPTION OF THE DRAWINGS

FIG. 6 sets forth a flow chart illustrating another example method for manufacturing a coplanar antenna circuit, according to embodiments of the present disclosure; and FIG. 7 sets forth a flow chart illustrating another example method for manufacturing a coplanar antenna circuit, according to embodiments of the present disclosure.

DETAILED DESCRIPTION OF EXAMPLE EMBODIMENTS

Figure 1A:
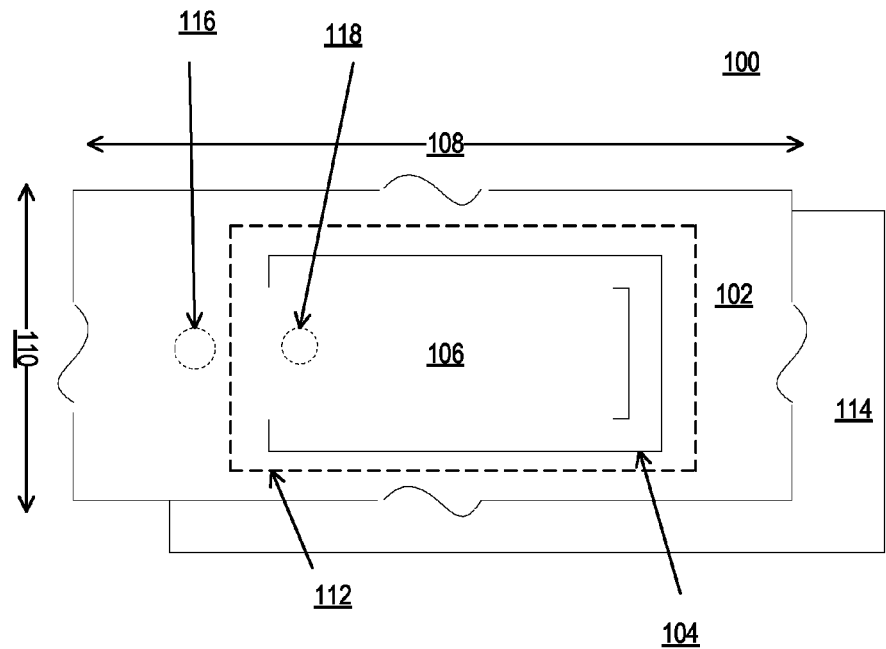
FIG. 1A sets forth an example simplified diagram of a coplanar antenna, according to embodiments of the present disclosure.

Example coplanar antennas, methods of operating coplanar antennas, personal sensor bracelets that include coplanar antennas and methods for manufacturing coplanar antenna circuits in accordance with the present disclosure are described with reference to the accompanying drawings, beginning with FIG. 1A. FIG. 1A sets forth an example simplified diagram of a coplanar antenna (100), according to embodiments of the present disclosure. In some embodiments, coplanar antenna (100) includes conductive plane (102) coupled to a conductive peninsula (106). Conductive plane (102) is separated from conductive peninsula (106) by insulating region (104).

In some current antennas, a planar inverted "F"-type antenna for example, a conductive, radiating element may be coupled to a ground plane via a conductive structure. The radiating element may then be "fed," or supplied, with an electrical signal from an electrical feed circuit through a feed point. The electrical feed circuit is a circuit configured to provide an electrical signal to the radiating element. By contrast, in example coplanar antenna (100), the radiating element may be considered to be conductive plane (102) in conjunction with the electrical properties provided by conductive peninsula (106), insulating region (104), and any additional electrical components provided by electrical feed circuit (114) that is electrically coupled to conductive plane (102) and conductive peninsula (106), as described in more detail below.

Conductive plane (102) may be comprised of any appropriate conductive material. For example, conductive plane (102) may comprise brass, gold, copper, etc., and/or alloys containing appropriate conductive materials. Conductive plane (102) extends along two dimensions: first dimension (108) and second dimension (110). In some current antennas, the length of the radiating element is chosen to be approximately one-quarter of a resonant frequency (the frequency at which the antenna is expected to operate). The size of conductive plane (102) may be selected such that its length along first dimension (108) is less than one-quarter of the resonant frequency wavelength. As described in more detail below, due to the inclusion of conductive peninsula (106), this may allow for coplanar antenna (100) to operate at a relatively higher resonant frequency than may be expected given the chosen size of conductive plane (102).

Conductive peninsula (106) may be comprised of any appropriate conductive material. For example, conductive peninsula (106) may comprise brass, gold, copper, etc., and/or alloys containing appropriate conductive materials. In some embodiments, conductive peninsula (106) may be formed from an integral piece of conductive material with conductive plane (102). For example, a sheet of brass may be cut in such a manner as to leave conductive peninsula (106) separated from conductive plane (102), as illustrated in FIG. 1A. In alternative embodiments, conductive peninsula (106) may be formed of a different material than conductive plane (102). For example, conductive plane (102) may be formed of a first material (e.g., gold) and conductive peninsula (106) may be formed of a second material (e.g., copper), and the two may be coupled to one another by an appropriate bonding mechanism.

Conductive peninsula (106) may have a shape generally outlined by insulating region (104). Insulating region (104) is a region disposed within conductive plane (102) such that insulating region (104) is substantially filled with an insulating material. For example, insulating region (104) may be an air gap between conductive plane (102) and conductive peninsula (106). Depending on the final configuration of coplanar antenna (100) and/or its inclusion in particular products, the material chosen to fill insulating region (104) may vary. As noted above, insulating region (104) may be left as an air gap. In other configurations, insulating region (104) may be filled with a dielectric material such as a plastic resin or other appropriate dielectric material.

In some embodiments, conductive plane (102) may include a major portion (112) that is substantially planar. In these embodiments, conductive peninsula (106) and insulating region (104) are substantially coplanar with major portion (112) of conductive plane (102). As described in more detail below with reference to FIGS. 2-3, conductive plane (102) may include other portions that curve or bend away from the planarity of major portion (112). For example, coplanar antenna (100) may be incorporated into a wearable device (e.g., a bracelet), and portions of conductive plane (102) may be formed to curve in accordance with the appropriate form factor.

In order to operate, or resonate, at a desired frequency, conductive plane (102) and conductive peninsula (106) are electrically coupled to electric feed circuit (114) via electrical connections (116) and (118), respectively. As described in more detail below, a current is supplied to conductive plane (102) and conductive peninsula (106) via electrical connections (116) and (118) from electric feed circuit (114).

In some embodiments, the current applied to conductive peninsula (106) does not result in conductive peninsula (106) becoming a radiating element. That is, conductive peninsula (106) does not substantially resonate at the frequency desired by the operation of coplanar antenna (100). Rather, due to its separation from conductive plane (102) via insulating region (104), as well as the placement of electrical connection (118), conductive peninsula (106) acts to provide an inductance to the antenna circuit. This inductance, along with any additional appropriate components within electric feed circuit (114) (e.g., capacitors) allows for coplanar antenna (100) to be tuned to a particular resonant frequency. This tuning may be the result of design considerations regarding the shape, density, component materials, etc., chosen for conductive peninsula (106). Alternatively, tuning may be accomplished through the placement (and/or other design characteristics) of electrical connection (118). In alternative embodiments, the current applied to conductive peninsula (106) may result in conductive peninsula (106) becoming a radiating element, as described in more detail below.

Generally, this allows for coplanar antenna (100) to be configured in a manner than may be smaller in dimension that is typical for the desired resonant frequency. Due to the inductance provided by conductive peninsula (106), conductive plane (102) may be sized such that it is smaller (e.g., along first dimension (108)) than the typical one-quarter wavelength of the desired resonant frequency. The dimensions of conductive peninsula (106) may be chosen in order to provide the desired inductance value to the antenna circuit, and the size may thus vary in accordance with the desired design values (e.g., desired frequency, desired form factor size, etc.). The electrical resonant properties of coplanar antenna (100) may be further tuned by the addition of electrical components to electric feed circuit (114). One advantage of the present disclosure is that, by incorporating the relatively large inductance through the use of conductive peninsula (106), the tuning components of electric feed circuit (114) may be relatively small and incorporated directly onto a small printed circuit board, for example.

In some embodiments, coplanar antenna (100) may be sufficiently immune to electrostatic discharge concerns that no insulating cover (e.g., a radome) is required. In some current antenna designs, the antenna may be covered with a radome both to protect the electrical components of the antenna from electrostatic discharge, and to protect the electrical, resonant properties of the underlying antenna circuit. By contrast, coplanar antenna (100) does not require any insulating cover. In some embodiments, the elements of coplanar antenna (100) may be covered with an additional material in order to improve the appearance of coplanar antenna (100). For example, conductive plane (102) may be plated with gold or vanadium in order to improve its appearance when used, for example, in a wearable bracelet.

Figure 1B:
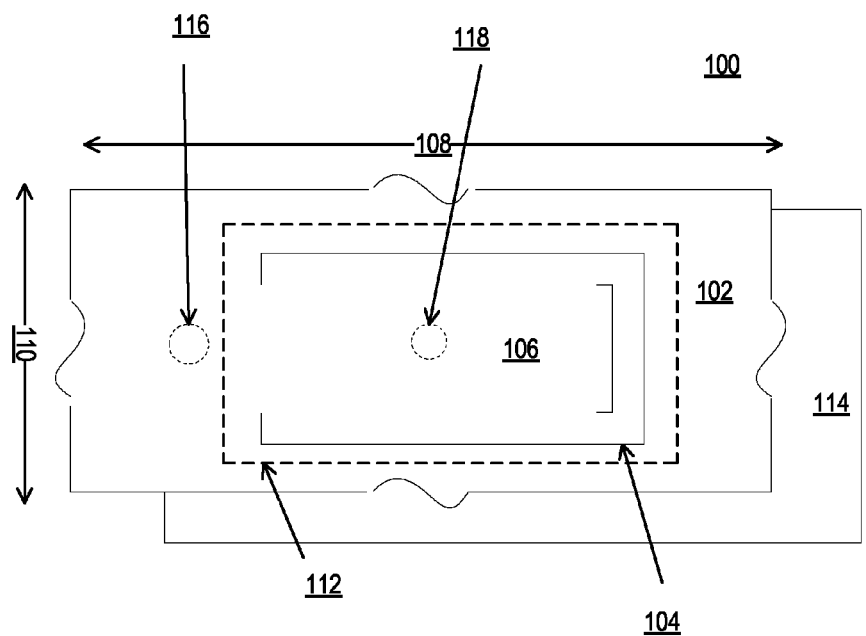
FIG. 1B sets forth an example simplified diagram of a coplanar antenna, according to embodiments of the present disclosure.

FIG. 1B sets forth an additional example simplified diagram of a coplanar antenna (100), according to embodiments of the present disclosure. In some embodiments, coplanar antenna (100) includes conductive plane (102) coupled to a conductive peninsula (106), as described in more detail above with reference to FIG. 1A. Conductive plane (102) is separated from conductive peninsula (106) by insulating region (104).

Conductive peninsula (106) may have a shape generally outlined by insulating region (104). Insulating region (104) is a region disposed within conductive plane (102) such that insulating region (104) is substantially filled with an insulating material. For example, insulating region (104) may be an air gap between conductive plane (102) and conductive peninsula (106). Depending on the final configuration of coplanar antenna (100) and/or its inclusion in particular products, the material chosen to fill insulating region (104) may vary. As noted above, insulating region (104) may be left as an air gap. In other configurations, insulating region (104) may be filled with a dielectric material such as a plastic resin or other appropriate dielectric material.

In some embodiments, conductive plane (102) may include a major portion (112) that is substantially planar. In these embodiments, conductive peninsula (106) and insulating region (104) are substantially coplanar with major portion (112) of conductive plane (102). As described in more detail below with reference to FIGS. 2-3, conductive plane (102) may include other portions that curve or bend away from the planarity of major portion (112). For example, coplanar antenna (100) may be incorporated into a wearable device (e.g., a bracelet), and portions of conductive plane (102) may be formed to curve in accordance with the appropriate form factor.

In order to operate, or resonate, at a desired frequency, conductive plane (102) and conductive peninsula (106) are electrically coupled to electric feed circuit (114) via electrical connections (116) and (118), respectively. As described in more detail below, a current is supplied to conductive plane (102) and conductive peninsula (106) via electrical connections (116) and (118) from electric feed circuit (114).

In some embodiments, the current applied to conductive peninsula (106) may result in conductive peninsula (106) becoming a radiating element. That is, conductive peninsula (106) does substantially resonate at the frequency desired by the operation of coplanar antenna (100). This may be accomplished, for example, by positioning electrical connection (118) at a point along dimension (108) distal from electrical connection (116). When a current is provided to electrical connection (118), a circuit including electrical connection (118) may see an impedance associated with conductive peninsula (106). The closer that electrical connection (118) is placed to electrical connection (116), the lower that impedance will be (e.g., electrical connection (116) may be at a zero-ohm impedance level by virtue of its connection to electric feed circuit (114). Likewise, the further that electrical connection (118) is placed to electrical connection (116), the higher that impedance may be.

In order to configure conductive peninsula (106) as a radiating element at a desired frequency, the impedance seen by the antenna circuit at electrical connection (116) may need to be substantially matched to the impedance provided by the source of the radio signal provide to antenna (100). For example, antennas usually operate at a fifty-ohm impedance matching. By placing electrical connection (118) at a point on conductive peninsula (106) along dimension (108) distal from electrical connection (116) such that the impedance seen at electrical connection (118) is the desired impedance for radio operation, conductive peninsula (106) may be configured so as to resonate at a desired frequency. The exact placement of electrical connection (118) along conductive peninsula (106) may vary depending on various design considerations including the shape, density, material, etc., of conductive peninsula (106), the desired resonant frequency, the desired impedance matching, etc. Therefore, although an example configuration is illustrated in FIG. 1B, variations may be present in any given configuration without departing from the scope of the present disclosure. Further, electric feed circuit (114) may include any additional appropriate components (e.g., capacitors) in order for coplanar antenna (100) to be tuned to a particular resonant frequency.

Figure 2:
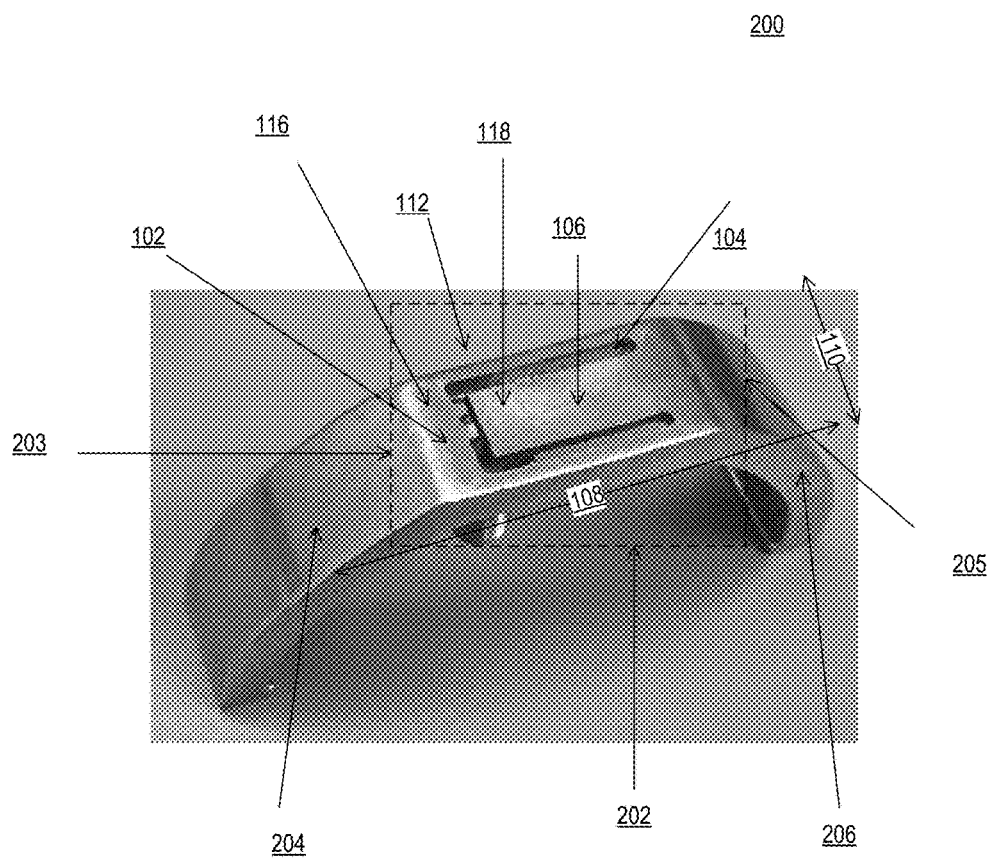
FIG. 2 illustrates an example curved conductive band incorporating a coplanar antenna, in accordance with certain embodiments of the present disclosure.

FIG. 2 illustrates an example curved conductive band (200) incorporating coplanar antenna (100), in accordance with certain embodiments of the present disclosure. In some embodiments, curved conductive band (200) may include a substantially planar portion (202) having a first end (203) and a second end (205). Extending from first end (203) is first curved portion (204), and extending from second end (205) is second curved portion (206). These structural portions of curved conductive band (200) may be configured in such a manner as to provide a wearable electronic device incorporating coplanar antenna (100).

In some embodiments, the wearable electronic device may be a bracelet. In some configurations, the bracelet may have a structure that is composed of a generally round or ovular shape composed primarily of first curved portion (204) and second curved portion (206). First curved portion (204) and second curved portion (206) may be formed of an integral piece of a conductive material (e.g., bronze, gold, etc.). In alternative embodiments, first curved portion (204) and second curved portion (206) may be formed of different materials. In still other embodiments, first curved portion (204) and second curved portion (206) may be coupled to one another either removably (e.g., via a clasp or other coupling mechanism) or fixedly. In still other embodiments, curved conductive band (200) may be part of a larger wearable electronic device.

Figure 3:
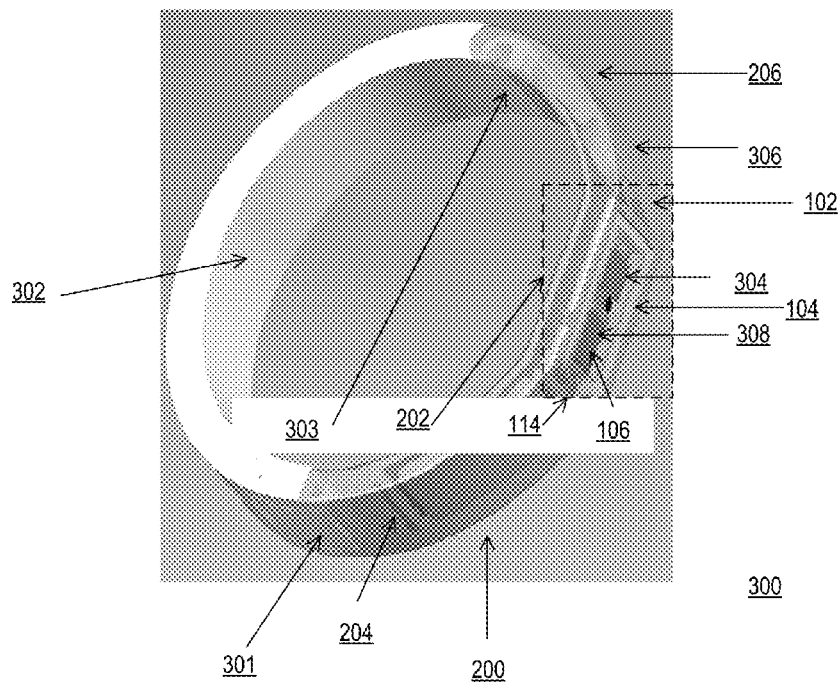
FIG. 3 illustrates an example personal sensor bracelet incorporating a curved conductive band, in accordance with certain embodiments of the present disclosure.

FIG. 3 illustrates an example personal sensor bracelet (300) incorporating curved conductive band (200), in accordance with certain embodiments of the present disclosure. Personal sensor bracelet (300) includes curved conductive band (200) coupled to a second curved band (302) removably coupled to curved conductive band (200) in order to form a generally circular or ovular bracelet. In some embodiments, personal sensor bracelet (300) also includes a processor (304) and a plurality of sensors (306) electrically coupled to electric feed circuit (114) and disposed within the substantially planar portion (202) of curved conductive band (200).

As described in more detail above with reference to FIGS. 1-2, substantially planar portion (202) of curved conductive band (200) may have disposed within it major portion (104) of coplanar antenna (100). In addition, electric feed circuit (114) may also be disposed within substantially planar portion (202) of curved conductive band (200). In order to provide intelligence to electric feed circuit (114) and coplanar antenna (100), personal sensor bracelet (300) may also have processor (304) and plurality of sensors (306) disposed within substantially planar portion (202) of curved conductive band (200). In some embodiments, electric feed circuit (114), processor (304), and plurality of sensors (306) may be included on a single component carrier (e.g., a printed circuit board) disposed within substantially planar portion (202) of curved conductive band (200).

In some embodiments, sensors (306) may be one or more appropriate sensors configured to collect environmental data about the environment in which personal sensor bracelet (300) is found. For example, sensors (306) may be configured to collect atmospheric data (e.g., time, duration, temperature, humidity, etc.), logistical data (e.g., position, distance travelled, etc.), biometric data (e.g., heart rate, body composition, blood pressure, etc.), and other environmental data. In order to store this data, whether temporarily or permanently, personal sensor bracelet may include one or more types of memory (308). Memory (308) may also be used to store computer-readable program instructions that may be carried out by processor (304).

For example, memory (308) may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a random access memory (RAM), a read-only memory (ROM), an erasable programmable read-only memory (EPROM or Flash memory), a static random access memory (SRAM), and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on processor (304), partly on processor (304), as a stand-alone software package, partly on processor (304) and partly on a remote computer or entirely on the remote computer or server.

In the latter scenario, the remote computer may be connected to processor (304) a network operating on the resonant frequency of coplanar antenna (100), or the connection may be made to an external computer (for example, through the Internet using an Internet Service Provider). In some embodiments, processor (304) may be communicatively coupled to the external computer by means of a relatively direct electrical connection (e.g., a universal serial bus ("USB") connection). In some embodiments, the external computer may be a personal computer, network server, tablet computer, web application, smart phone, personal digital assistant, or any other appropriate electronic device operable to retrieve and/or send data to and from memory (308).

In operation, personal sensor bracelet (300) may be operable to collect a variety of environmental data associated with the user of personal sensor bracelet (300) and transmit, via coplanar antenna (100), that environmental data to one or more software modules for further analysis. The user may then access the transmitted data in real-time, near real-time, and/or a later time through one or more user interfaces to the analysis software. For example, the user may access a smart phone app in order to view the environmental data.

In some embodiments, in addition to the intelligence provided by processor (304), sensors (306), and memory (308), personal sensor bracelet (300) may also include second curved band (302) removably coupled to curved conductive band (200) in order to form a generally circular or ovular bracelet. Second curved band (302) may be removably coupled to curved conductive band (200) at an end (301) of first curved portion (204) distal from the substantially planar portion (202) of curved conductive band (200) and/or removably coupled to curved conductive band (200) at and end (303) of second curved portion (206) distal from the substantially planar portion (206) of curved conductive band (200). In some embodiments, the mechanism for coupling one or more portions of second curved band (302) to curved conductive band (200) may be a clasp (e.g., to unattach one end of second curved band (302) in order for a user to more comfortably attach personal sensor bracelet (300)), a detachable hinge (e.g., a hinged portion at one end for use in attaching personal sensor bracelet (300) to a user, wherein the hinge may be fully removed in order to change out second curved band (302) as described in more detail below), or other appropriate mechanism.

One advantage of incorporating second curved band (302) into personal sensor bracelet (300) is to provide flexibility in the design of personal sensor bracelet (300). For example, second curved band (302) may include different materials than those used for curved conductive band (200), which may reduce manufacturing costs. Additionally, second curved band (302) may include materials that are relatively more aesthetically appealing than the conductive material from which curved conductive band (200) is formed. For example, second curved band (302) may include materials of different colors (e.g., enamels, plastics, etc. in various colors) than may be available for use in curved conductive band (200). Further, the manner in which second curved band (302) is removably coupled to curved conductive band (200) may allow for a user to incorporate a plurality of second curved bands (302) in succession in order to alter the appearance of personal sensor bracelet (300). The relatively lower cost of second curved band (302) (in configurations in which second curved band (302) is formed from relatively inexpensive materials) may allow a user to alter the appearance of personal sensor bracelet (300) at a lower cost.

As described in more detail above with reference to FIGS. 1-2, coplanar antenna (100) may not be covered with a protective insulating cover (e.g., a radome). However, in order to improve the appearance of personal sensor bracelet (300), some or all of coplanar antenna (100) and/or curved conductive band (200) may be covered with an additional conductive material. For example, curved conductive band (200) may be plated with gold or vanadium in order to improve its aesthetic appearance and/or electrical characteristics. Further, in some embodiments, some aesthetic modifications may be made to coplanar antenna (100) and/or curved conductive band (200) may be made without departing from the scope of the present disclosure. For example, an etch may be made along the portion of curved conductive band (200) at which conductive peninsula (106) is coupled to conductive plane (102). This may be done to provide the appearance of a rectangular shape (e.g., the shape of insulating region (104), completed by the etch), which may then be filled by an appropriate material (e.g., jeweler's grout) to provide a relatively uniform appearance.

Further, although no insulating cover is required, some embodiments of the present disclosure may include decorative aspects added to some portion of coplanar antenna (100). For example, an emblem, jewel, label, or other object made of insulating material may be placed over a portion of coplanar antenna (e.g., in the center of conductive peninsula (106) in order to improve its aesthetic appearance. Such an object should not be understood to be the protective covering described above with reference to FIGS. 1-3.

Figure 4:
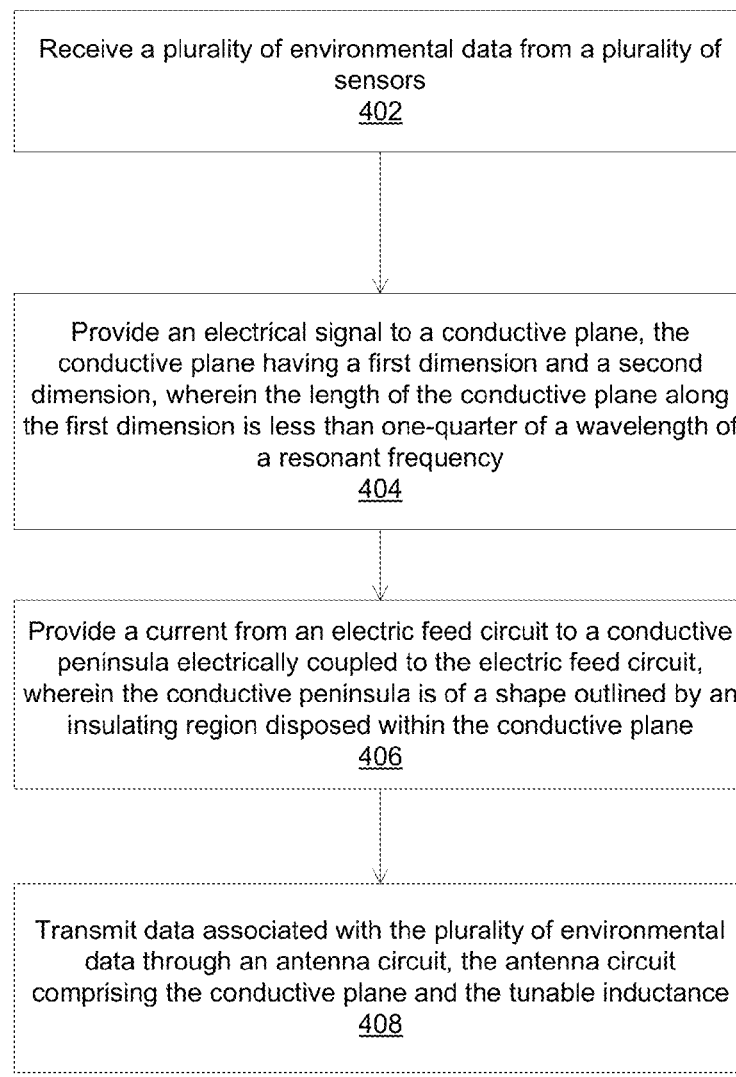
FIG. 4 sets forth a flow chart illustrating an example method for operating a coplanar antenna circuit, according to embodiments of the present disclosure.

For further explanation, FIG. 4 sets forth a flow chart illustrating an example method (400) for operating a coplanar antenna circuit, according to embodiments of the present disclosure. The example method (400) of FIG. 4 includes receiving (402) a plurality of environmental data from a plurality of sensors. For example, as described in more detail above with reference to FIG. 3, a device including coplanar antenna (100) (e.g., personal sensor bracelet (300)) may include a plurality of sensors (306). These sensors (306) may be operable to receive a variety of environmental data associated with a user of the device. For example, sensors (306) may be operable to receive atmospheric data, location data, biometric data, etc. As described in more detail above with reference to FIG. 3, this data may be stored in memory (308).

Also included in example method (400) is providing (404) an electrical signal to conductive plane (102), conductive plane (102) having a first dimension and a second dimension, wherein the length of conductive plane (102) along the first dimension is less than one-quarter of a wavelength of a resonant frequency. For example, as described above with reference to FIGS. 1-3, coplanar antenna (100) may include conductive plane (102), which may be configured to be of a shape that includes a length less than one-quarter of a wavelength of a desired resonance frequency. As described in more detail above with reference to FIG. 3, electric feed circuit (114) may be operable to provide an electric signal to conductive plane (102), resulting in conductive plane (102) resonating at the desired resonant frequency. Variations in this electric signal will result in variations in resonance of conductive plane (102), which may result in conductive plane (102) transmitting a signal associated with the electric signal provided by electric feed circuit (114). This may be done in accordance with known techniques of providing an electric signal to a resonant antenna in order to convert an electrical signal to a radio frequency ("RF") signal. In such a manner, antenna (100) may transmit data associated with the electric signal provided by electric feed circuit (114) via an RF signal.

Also included in method (400) is providing (406) a current from electric feed circuit (114) to conductive peninsula (106) electrically coupled to electric feed circuit (114), wherein conductive peninsula (106) is of a shape outlined by insulating region (104) disposed within conductive plane (102). As described in more detail above with reference to FIGS. 1-3, conductive peninsula (106) is coupled to conductive plane (102). Further conductive peninsula (106) is substantially coplanar to major portion (112) of conductive plane (102). Still further, conductive peninsula (106) is operable to electrically couple a tunable inductance to conductive plane (102) after receiving the current from electric feed circuit (114). For example, by providing a current from electric feed circuit (114) to conductive peninsula (106), conductive peninsula (106) may exhibit electrical characteristics that enable conductive peninsula (106) to provide an inductance to an antenna circuit comprising conductive plane (102), conductive peninsula (106), and electric feed circuit (114). The inductance provided by conductive peninsula (106) may be tuned through a variety of measures. For example, the dimensions of conductive peninsula (106) may be altered in a design phase to alter the inductance value provided by conductive peninsula (106). As an additional example, the materials comprising conductive peninsula (106) may be altered to alter the electric characteristics of conductive peninsula (106). As a further example, the current provided to conductive peninsula (106) by electric feed circuit (114) may be varied in order to more finely tune the inductance provided by conductive peninsula (106). With regard to this latter example, the current provided by electric feed circuit (114) to conductive peninsula (106) may be varied during operation to alter the inductance in accordance with varying needs of the antenna circuit (e.g., to switch operating bands/frequencies).

By including the variable inductance provided by conductive peninsula (106) in the antenna circuit, conductive plane (102) may be formed to be of a size less than one-quarter of a wavelength of a resonant frequency associated with antenna (100), as described in more detail above with reference to FIGS. 1-3. Further, as described in more detail above with reference to FIGS. 1-3, by including a relatively large inductance through the operation of conductive peninsula (106), additional tuning components associated with electric feed circuit (114) may be formed with relatively smaller components. For example, small capacitors may be included on electric feed circuit (114) in order to fine tune the operation of antenna (100).

Also included in example method (400) is transmitting (408) data associated with the plurality of environmental data through an antenna circuit, the antenna circuit comprising conductive plane (102) and the tunable inductance provided by conductive peninsula (106). For example, after receiving the environmental data from plurality of sensors (306), that data may be temporarily stored on memory (308). In some embodiments, processor (304) may then be operable to retrieve the data from memory (308) and cause an electric signal to be provided to conductive plane (102), as described in more detail above. This electric signal will be associated with the data retrieved from memory (308). Accordingly, data associated with the environmental data may be transmitted by conductive plane (102), conductive plane (102) being part of the antenna circuit including the tunable inductance provided by conductive peninsula (106) and electric feed circuit (114), as described in more detail above.

Figure 5:
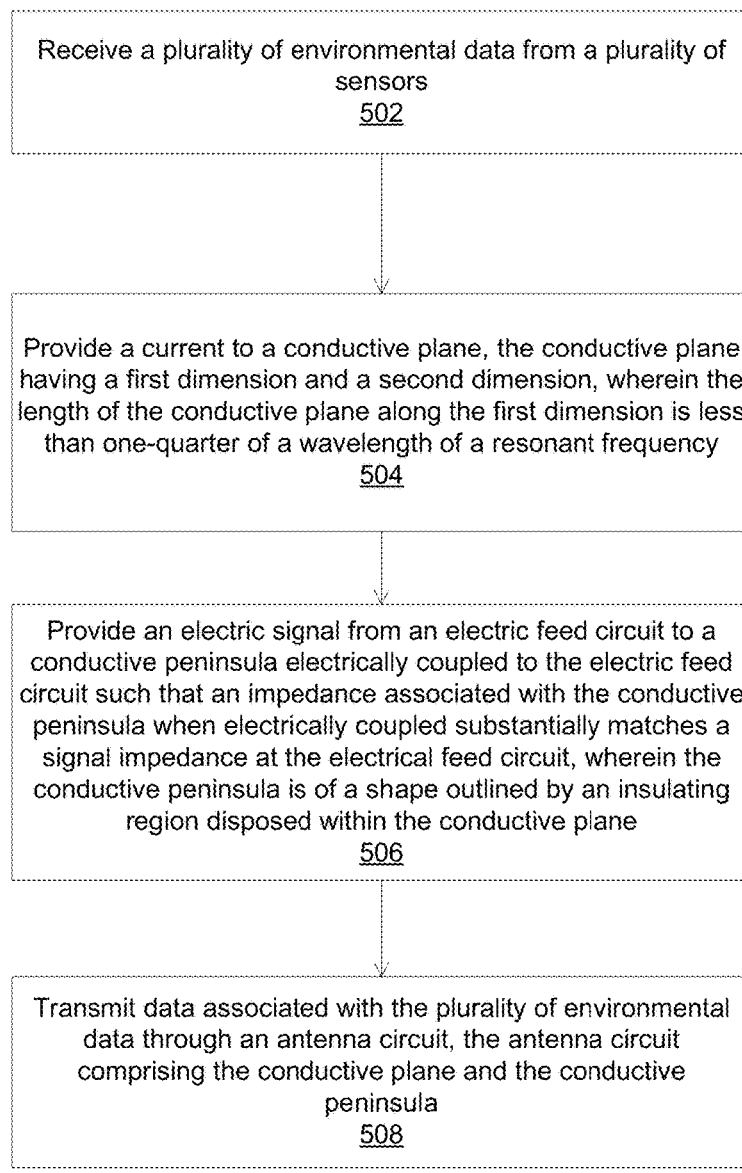
FIG. 5 sets forth a flow chart illustrating another example method for operating a coplanar antenna circuit, according to embodiments of the present disclosure.

For further explanation, FIG. 5 sets forth a flow chart illustrating another example method (500) for operating a coplanar antenna circuit, according to embodiments of the present disclosure. As described in more detail above with reference to FIGS. 1A-1B, antenna (100) may be configured in such a manner so that conductive peninsula (106) either acts as a tunable inductance or as a resonant element. Example method (500) is similar to example method (400), however example method (500) includes conductive peninsula (106) configured to act as a resonant element.

The example method (500) of FIG. 5 includes receiving (502) a plurality of environmental data from a plurality of sensors. For example, as described in more detail above with reference to FIG. 3, a device including coplanar antenna (100) (e.g., personal sensor bracelet (300)) may include a plurality of sensors (306). These sensors (306) may be operable to receive a variety of environmental data associated with a user of the device. For example, sensors (306) may be operable to receive atmospheric data, location data, biometric data, etc. As described in more detail above with reference to FIG. 3, this data may be stored in memory (308).

Also included in example method (500) is providing (504) a current to conductive plane (102), conductive plane (102) having a first dimension and a second dimension, wherein the length of conductive plane (102) along the first dimension is less than one-quarter of a wavelength of a resonant frequency. For example, as described above with reference to FIGS. 1-3, coplanar antenna (100) may include conductive plane (102), which may be configured to be of a shape that includes a length less than one-quarter of a wavelength of a desired resonance frequency. As described in more detail above with reference to FIG. 3, electric feed circuit (114) may be operable to provide a current to conductive plane (102), resulting in conductive plane (102) resonating at the desired resonant frequency. Variations in this electric signal will result in variations in resonance of conductive plane (102), which may result in conductive plane (102) transmitting a signal associated with the electric signal provided by electric feed circuit (114). This may be done in accordance with known techniques of providing an electric signal to a resonant antenna in order to convert an electrical signal to a radio frequency ("RF") signal. In such a manner, antenna (100) may transmit data associated with the electric signal provided by electric feed circuit (114) via an RF signal.

Also included in method (500) is providing (506) an electric signal from an electric feed circuit (114) to a conductive peninsula (106) electrically coupled to the electric feed circuit (114), such that an impedance associated with the conductive peninsula (106) when electrically coupled substantially matches a signal impedance at the electrical feed circuit (114), wherein the conductive peninsula (106) is of a shape outlined by an insulating region disposed within the conductive plane (102). As described in more detail above with reference to FIGS. 1-3, conductive peninsula (106) is coupled to conductive plane (102). Further conductive peninsula (106) is substantially coplanar to major portion (112) of conductive plane (102). Still further, conductive peninsula (106) is operable to substantially resonate at a desired frequency after receiving the current from electric feed circuit (114), as described in more detail above with reference to FIG. 1B.

Also included in example method (500) is transmitting (508) data associated with the plurality of environmental data through an antenna circuit, the antenna circuit comprising conductive plane (102) and conductive peninsula (106). For example, after receiving the environmental data from plurality of sensors (306), that data may be temporarily stored on memory (308). In some embodiments, processor (305) may then be operable to retrieve the data from memory (308) and cause an electric signal to be provided to conductive plane (102), as described in more detail above. This electric signal will be associated with the data retrieved from memory (308). Accordingly, data associated with the environmental data may be transmitted by conductive plane (102), conductive plane (102) being part of the antenna circuit including conductive peninsula (106) and electric feed circuit (114), as described in more detail above.

For further explanation, FIG. 6 sets forth a flow chart illustrating another example method (600) for manufacturing a coplanar antenna circuit, according to embodiments of the present disclosure. The example method (600) of FIG. 6 includes forming (602) conductive plane (102) from a first conductive material, conductive plane (102) having a first dimension (108) and a second dimension (110), wherein the length of conductive plane (102) along first dimension (108) is less than one-quarter of a wavelength of a resonant frequency. As described in more detail above with reference to FIG. 1A, forming (602) conductive plane (102) from a first conductive material may include forming conductive plane (102) from any appropriate conductive material such as bronze, copper, aluminum, gold, etc. Forming (602) conductive plane (102) may include taking into consideration a variety of design considerations, which may vary depending on the particular configuration desired. For example, the material chosen may be based on weight considerations, performance considerations, cost considerations, etc. Further, the exact dimensions of conductive plane (102) may vary depending on design considerations including performance considerations (e.g., the desired resonance frequency), size considerations (e.g., the desired size of the resultant personal device), etc. One of ordinary skill in the art would be able to determine the particular dimensions of conductive plane (102), and particular variations may be present without departing from the scope of the present disclosure.

Example method (600) also includes forming (602) conductive peninsula (106) from a second conductive material, conductive peninsula (106) being coupled to conductive plane (102) and separated from conductive plane (102) by insulating region (104), wherein conductive peninsula (106) is substantially coplanar to major portion (112) of conductive plane (102). As described in more detail above with reference to FIG. 1A, forming (604) conductive peninsula (106) from a second conductive material may include forming conductive peninsula (106) from any appropriate conductive material such as bronze, copper, aluminum, gold, etc.

Forming conductive peninsula (106) may include taking into consideration a variety of design considerations, which may vary depending on the particular configuration desired. For example, the material chosen may be based on weight considerations, performance considerations, cost considerations, etc. Further, the exact dimensions of conductive peninsula (106) may vary depending on design considerations including performance considerations (e.g., the desired resonance frequency), size considerations (e.g., the desired size of the resultant personal device), etc. Still further, as described in more detail above with reference to FIGS. 1-4, the exact dimensions of conductive peninsula (106) may be chosen in order to provide a particular inductance value to antenna (100). One of ordinary skill in the art would be able to determine the particular dimensions of conductive plane (102), and particular variations may be present without departing from the scope of the present disclosure.

Example method (600) also includes electrically coupling (606) conductive peninsula (106) to electric feed circuit (114), wherein conductive peninsula (106) is operable to electrically couple a tunable inductance to conductive plane (102) after receiving a current from electric feed circuit (114). In some embodiments, conductive peninsula (106) and conductive plane (102) may be formed from an integral piece of the same conductive material. In such embodiments, the first and second conductive materials may be substantially the same. In alternative embodiments, conductive peninsula (106) and conductive plane (102) may be formed from different pieces of conductive material and coupled together through any appropriate coupling mechanism, as would be apparent to one of ordinary skill in the art.

For further explanation, FIG. 7 sets forth a flow chart illustrating another example method (700) for manufacturing a coplanar antenna circuit, according to embodiments of the present disclosure. As described in more detail above with reference to FIGS. 1A-1B, antenna (100) may be configured in such a manner so that conductive peninsula (106) either acts as a tunable inductance or as a resonant element. Example method (700) is similar to example method (600), however example method (700) includes conductive peninsula (106) configured to act as a resonant element.

The example method (700) of FIG. 7 includes forming (702) conductive plane (102) from a first conductive material, conductive plane (102) having a first dimension (108) and a second dimension (110), wherein the length of conductive plane (102) along first dimension (108) is less than one-quarter of a wavelength of a resonant frequency. As described in more detail above with reference to FIG. 1A, forming (702) conductive plane (102) from a first conductive material may include forming conductive plane (102) from any appropriate conductive material such as bronze, copper, aluminum, gold, etc. Forming (702) conductive plane (102) may include taking into consideration a variety of design considerations, which may vary depending on the particular configuration desired. For example, the material chosen may be based on weight considerations, performance considerations, cost considerations, etc. Further, the exact dimensions of conductive plane (102) may vary depending on design considerations including performance considerations (e.g., the desired resonance frequency), size considerations (e.g., the desired size of the resultant personal device), etc. One of ordinary skill in the art would be able to determine the particular dimensions of conductive plane (102), and particular variations may be present without departing from the scope of the present disclosure.

Example method (700) also includes forming (702) conductive peninsula (106) from a second conductive material, conductive peninsula (106) being coupled to conductive plane (102) and separated from conductive plane (102) by insulating region (104), wherein conductive peninsula (106) is substantially coplanar to major portion (112) of conductive plane (102). As described in more detail above with reference to FIG. 1B, forming (704) conductive peninsula (106) from a second conductive material may include forming conductive peninsula (106) from any appropriate conductive material such as bronze, copper, aluminum, gold, etc.

Forming conductive peninsula (106) may include taking into consideration a variety of design considerations, which may vary depending on the particular configuration desired. For example, the material chosen may be based on weight considerations, performance considerations, cost considerations, etc. Further, the exact dimensions of conductive peninsula (106) may vary depending on design considerations including performance considerations (e.g., the desired resonance frequency), size considerations (e.g., the desired size of the resultant personal device), etc. Still further, as described in more detail above with reference to FIGS. 1-4, the exact dimensions of conductive peninsula (106) may be chosen in order to provide a particular resonant frequency value to antenna (100). One of ordinary skill in the art would be able to determine the particular dimensions of conductive plane (102), and particular variations may be present without departing from the scope of the present disclosure.

Example method (700) also includes electrically coupling (706) conductive peninsula (106) to electric feed circuit (114), wherein conductive peninsula (106) is operable to substantially resonate at a frequency after receiving a current from electric feed circuit (114). In some embodiments, conductive peninsula (106) and conductive plane (102) may be formed from an integral piece of the same conductive material. In such embodiments, the first and second conductive materials may be substantially the same. In alternative embodiments, conductive peninsula (106) and conductive plane (102) may be formed from different pieces of conductive material and coupled together through any appropriate coupling mechanism, as would be apparent to one of ordinary skill in the art.

The flowcharts in the Figures illustrate the architecture, functionality, and operation of possible implementations of systems and methods according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will be understood from the foregoing description that modifications and changes may be made in various embodiments of the present disclosure without departing from its true spirit. The descriptions in this specification are for purposes of illustration only and are not to be construed in a limiting sense. The scope of the present disclosure is limited only by the language of the following claims.

What is claimed is:

1. A coplanar antenna comprising:
   a wearable conductive plane having a first dimension and a second dimension, wherein the length of the conductive plane along the first dimension is less than one-quarter of a wavelength of a resonant frequency;

an insulating region disposed within the conductive plane, the disposition of the insulating region defining a conductive peninsula within the conductive plane, wherein:
- the conductive peninsula is electrically coupled directly to the conductive plane and separated on three sides from the conductive plane by the insulating region;
- the conductive peninsula is substantially coplanar to a major portion of the conductive plane;
- the conductive peninsula is electrically coupled to an electric feed circuit such that an impedance associated with the conductive peninsula when electrically coupled substantially matches a signal impedance at the electrical feed circuit; and
- the conductive peninsula is operable to resonate at the resonant frequency after receiving a current from the electric feed circuit;

a first electrical connection that electrically couples the conductive plane to the electric feed circuit; and a second electrical connection that electrically couples the conductive peninsula to the electric feed circuit, and wherein the first electrical connection is positioned at a point along the first dimension distal from the second electrical connection.

2. The coplanar antenna of claim 1, wherein the conductive plane and the conductive peninsula are formed from an integral piece of conductive material.

3. The coplanar antenna of claim 1, wherein the conductive plane is not covered by an insulating radome in operation.

4. The coplanar antenna of claim 1, wherein the insulating region is formed by removing a portion of the conductive plane.

5. The coplanar antenna of claim 1, wherein the insulating region is substantially filled by a dielectric material.

6. The coplanar antenna of claim 1, wherein the electric feed circuit comprises a tuning circuit operable to electrically compensate for a portion of the wavelength of the resonant frequency.

7. The coplanar antenna of claim 1, wherein the conductive plane is electrically coupled to the electric feed circuit.

8. The coplanar antenna of claim 1, wherein the insulating region is disposed between an interior of the conductive plane and an exterior of the conductive peninsula.

9. A method of manufacturing a coplanar antenna circuit, the method comprising:
- forming a wearable conductive plane from a first conductive material, the conductive plane having a first dimension and a second dimension, wherein the length of the conductive plane along the first dimension is less than one-quarter of a wavelength of a resonant frequency;
- forming from a second conductive material a conductive peninsula within the conductive plane and substantially coplanar to a major portion of the conductive plane, the conductive peninsula being electrically coupled directly to the conductive plane and separated on three sides from the conductive plane by an insulating region that defines the conductive peninsula; and
- electrically coupling the conductive peninsula to an electric feed circuit, wherein the conductive peninsula is operable to resonate at the resonant frequency after receiving a current from the electric feed circuit, and wherein the conductive plane and the conductive peninsula are electrically coupled to the electric feed circuit via a first electrical connection and a second electrical connection and the first electrical connection is positioned at a point along the first dimension distal from the second electrical connection.

* * * * *